United States Patent
Tanaka et al.

(10) Patent No.: US 8,840,585 B2
(45) Date of Patent: Sep. 23, 2014

(54) MOTORIZED SYRINGE FOR USE WITH TWO TYPES OF DENTAL ANESTHETIC SOLUTION-CONTAINING CARTRIDGES

(75) Inventors: Fumio Tanaka, Kawasaki (JP); Mitsuhiro Haraguchi, Shiraoka (JP); Yoshihiko Kawasaki, Tokyo (JP); Akiko Kawasaki, legal representative, Yokohama (JP); Mutsumi Shibuya, Yokohama (JP); Renji Hayashi, Matsudo (JP); Yoshinori Kato, Matsudo (JP)

(73) Assignee: Showa Yakuhin Kako Co., Ltd., Chuo-ku, Tokyo (JP)

( * ) Notice: Subject to any disclaimer, the term of this patent is extended or adjusted under 35 U.S.C. 154(b) by 0 days.

(21) Appl. No.: 14/009,752

(22) PCT Filed: Apr. 12, 2011

(86) PCT No.: PCT/JP2011/059089
§ 371 (c)(1),
(2), (4) Date: Oct. 3, 2013

(87) PCT Pub. No.: WO2012/140738
PCT Pub. Date: Oct. 18, 2012

(65) Prior Publication Data
US 2014/0023986 A1    Jan. 23, 2014

(51) Int. Cl.
| A61M 31/00 | (2006.01) |
| A61M 5/20 | (2006.01) |
| A61M 5/315 | (2006.01) |
| A61M 5/24 | (2006.01) |
| A61M 5/145 | (2006.01) |
| A61C 19/08 | (2006.01) |

(52) U.S. Cl.
CPC ............. *A61M 5/31583* (2013.01); *A61M 5/20* (2013.01); *A61M 5/24* (2013.01); *A61M 5/1452* (2013.01); *A61M 2005/2411* (2013.01); *A61C 19/08* (2013.01); *A61M 5/315* (2013.01)
USPC .......................................... 604/131; 604/154

(58) Field of Classification Search
CPC ... A61M 1/0005; A61M 1/0009; A61M 5/24; A61M 5/32
USPC ......... 604/110, 131, 132, 134–136, 139, 148, 604/154, 197, 232–234; 433/90; 128/DIG. 1, DIG. 12, DIG. 13
See application file for complete search history.

(56) References Cited

U.S. PATENT DOCUMENTS

| 7,476,216 B2 * | 1/2009 | Takatsuka et al. ............ 604/131 |
| 2004/0073168 A1 | 4/2004 | Takatsuka et al. |
| 2008/0097325 A1 | 4/2008 | Tanaka et al. |

FOREIGN PATENT DOCUMENTS

| JP | 2006-230701 A | 9/2006 |
| JP | 4198435 B2 | 12/2008 |

*Primary Examiner* — Theodore Stigell
*Assistant Examiner* — Amber Stiles
(74) *Attorney, Agent, or Firm* — Taft Stettinius & Hollister LLP

(57) ABSTRACT

A motorized syringe for use with two types of dental anesthetic solution-filled cartridges, having a plunger plug in the 1.8 ml cartridge pushed by a push rod by a length required to push a plunger plug in the 1.0 ml cartridge. The syringe includes a cartridge holder for use with 1.0 ml and 1.8 ml cartridges, the push rod having a 1.0 ml position and a 1.8 ml position drawn back from the 1.0 ml position so that push rod movement can end at a common terminal position for both, a sleeve adapted to receive the push rod rear end when pushed back from the common terminal position, and to be not interfered with by the push rod's rear end when it is in the 1.0 ml position, the sleeve being pushed rearward with the push rod's rear end when pushed back to the 1.8 ml position.

4 Claims, 4 Drawing Sheets

MOTORIZED SYRINGE FOR USE WITH TWO TYPES OF DENTAL ANESTHETIC SOLUTION-CONTAINING CARTRIDGES

TECHNICAL FIELD

The present invention relates to a motorized syringe adapted to be used in common for two types of cartridges containing 1.0 ml and 1.8 ml of anesthetic solution.

BACKGROUND OF THE INVENTION

Cartridges adapted to be used with such a motorized syringe are made of transparent glass and have dental anesthetic solution filled therein. There are two types of cartridges containing 1.8 ml and 1.0 ml of anesthetic solution, and due to the fact that the cartridges have the same inside and outside diameters, they are different in length. In the case of either cartridge, upon administrating anesthetic, a cartridge holder is connected to the motorized syringe by means of a coupling, the cartridge holder having the cartridge loaded therein, and a double pointed needle is attached to the forward end of the cartridge holder to bring it into communication with the interior of the cartridge.

The motorized syringe includes a push rod adapted to push a plunger rubber plug in the cartridge to deliver the anesthetic solution from the cartridge through the needle, and an operating device for moving the push rod forward. Such an operating device generally includes a pinion rotated through a power transmission from a drive unit including a motor and a reduction gear, and a rack formed on the push rod and engaging the rotating pinion to linearly move the push rod. In order to deliver the anesthetic solution from the cartridge loaded in the cartridge holder, the linear movement of the push rod must be performed for a distance equal to the length of accommodation of anesthetic solution in the cartridge. The distance of linear movement of the push rod is defined by bringing a limit switch into an off-state with a particular portion of the push rod to stop the rotation of the motor. After delivery of anesthetic solution, the cartridge holder is detached from the coupling, and the power transmission from the drive unit is interrupted to bring the pinion into an idle state. The push rod can thus be pushed into the syringe body by hand. In this process, the limit switch is brought into an on-state with the outer surface of the push rod.

A cartridge-type motorized syringe, as well as a cartridge holder and a push rod, which the applicant is presently manufacturing and selling to dentists, is arranged as a syringe for exclusive use of each of a 1.0 ml cartridge and a 1.8 ml cartridge since the distances required to push plunger rubber plugs in both the cartridges are different due to the difference in length between the 1.0 ml cartridge and the 1.8 ml cartridge. With the spread of motorized syringes, the appearance of a new motorized syringe capable of being used in common for both 1.0 ml and 1.8 ml cartridges has been desired by dentists. In order to realize their desire, bearing the arrangement of the conventional motorized syringe in mind, it is required to use a cartridge holder in common for both 1.0 ml cartridges and 1.8 ml cartridges, to establish a common terminal position of a push rod, with respect to 1.0 ml cartridges and 1.8 ml cartridges, and to draw back a start position of the push rod for the 1.8 ml cartridge by a distance equal to the difference in length between the 1.0 ml and 1.8 ml cartridges. Since the push rod has a length required to push a plunger rubber plug throughout the length of the 1.8 ml cartridge, it must extend rearward by a distance equal to the difference in length between the cartridges. For this reason, the motorized syringe body is compelled to have a rearward protrusive configuration. The invention made on the basis of this idea is disclosed in patent reference 1. This patent reference 1 also discloses that in either cartridge-setting position, a push rod is urged against a plunger rubber plug in a cartridge under a constant pressure. However, the invention disclosed in patent reference 1 is undesirable because it does not make a configuration of the motorized syringe compact.

Patent reference 1: U.S. Pat. No. 4,198,435

DISCLOSURE OF THE INVENTION

An object of the present invention is to provide a motorized syringe for use of two type of dental anesthetic solution-filled cartridges, including a cartridge holder configured to be used in common for both an anesthetic solution 1.0 ml cartridge and an anesthetic solution 1.8 ml cartridge, and a push rod of a length required to push a plunger rubber plug in the 1.0 ml cartridge, said syringe being arranged to be capable of pushing a plunger rubber plug in the 1.8 ml cartridge with the same push rod.

The object of the invention can be achieved by providing a motorized syringe for use with two types of dental anesthetic solution-filled cartridges, comprising a syringe body, a cartridge holder adapted to be connected to the syringe body by means of a coupling, the cartridge being loaded in the cartridge holder, a push rod having a rack formed thereon, and a pinion engaged with the rack and adapted to be rotated by a drive unit, the engagement of the rotating pinion with the rack permitting the push rod to be slowly moved forward, thereby pushing a plunger rubber plug in the anesthetic solution-filled cartridge for delivery of the anesthetic solution from the cartridge through a needle, characterized in that the cartridge holder is configured to be capable of being used in common for both 1.0 ml and 1.8 ml cartridges, the push rod has a 1.0 ml cartridge-setting position and a 1.8 ml cartridge-setting position drawn back from the 1.0 ml cartridge-setting position so that the movement of the push rod can end at a common terminal position for both 1.0 ml and 1.8 ml cartridges, and there is provided a bottomed sleeve adapted to receive the rear end portion of the push rod therein when the push rod is pushed back from the common terminal position, and to be not interfered with by the rear end face of the push rod when it is in the 1.0 ml cartridge-setting position, the sleeve being pushed rearward with the rear end face of the push rod when the push rod is pushed back to the 1.8 ml cartridge-setting position, and a return spring for moving the sleeve forward together with the push rod upon its forward movement.

In the motorized syringe according to the invention, the coil return spring is disposed around the bottomed sleeve and abuts at its one end a peripheral flange formed on the sleeve at its forward end, and at its other end abuts a shoulder in a bore formed in the syringe body at its rear end, to urge the sleeve against a side surface portion of the drive unit in a normal state thereof.

Further, in the motorized syringe according to the invention, the sleeve preferably has a length slightly longer than a difference in length between the 1.0 ml cartridge and the 1.8 ml cartridge.

Furthermore, in the motorized syringe according to the invention, the sleeve is adapted to protrude through the bore at the rear end of the syringe body when the sleeve is pushed rearward by the rear end face of the push rod.

According to the invention, either a 1.0 ml cartridge or a 1.8 ml cartridge is loaded into the cartridge holder, which is then connected to the motorized syringe by means of the coupling. The push rod is slowly moved forward by the rack engaged with the pinion rotated via the drive unit, so that it can push the plunger rubber plug in the anesthetic solution-filled cartridge to deliver the anesthetic solution from the cartridge through the needle. Since the movement of the push rod ends at the common terminal position for both the 1.0 ml cartridge and the 1.8 ml cartridge, the 1.8 ml cartridge-setting position draws back from the 1.0 ml cartridge-setting position by the deference in length between the cartridges. When the push rod is pushed back from the common terminal position, the bottomed sleeve receives the rear end portion of the push rod, and when the push rod is in the 1.0 ml cartridge-setting position, the sleeve remains in position without being pushed with the rear end face of the push rod. When the push rod is returned to the 1.8 ml cartridge-setting position, the sleeve is pushed rearward with the rear end face of the push rod so that the return spring is compressed. In the case of either cartridge, linear forward movement of the push rod causes the plunger rubber plug in the cartridge to be pushed, thereby delivering the anesthetic solution from the cartridge through the needle, and in the case of the 1.8 ml cartridge, the sleeve moves forward together with the push rod under the action of the return spring exerted on the peripheral flange thereof, until it abuts against the portion of the drive unit.

BEST MODE FOR CARRYING OUT THE INVENTION

Figure 1:
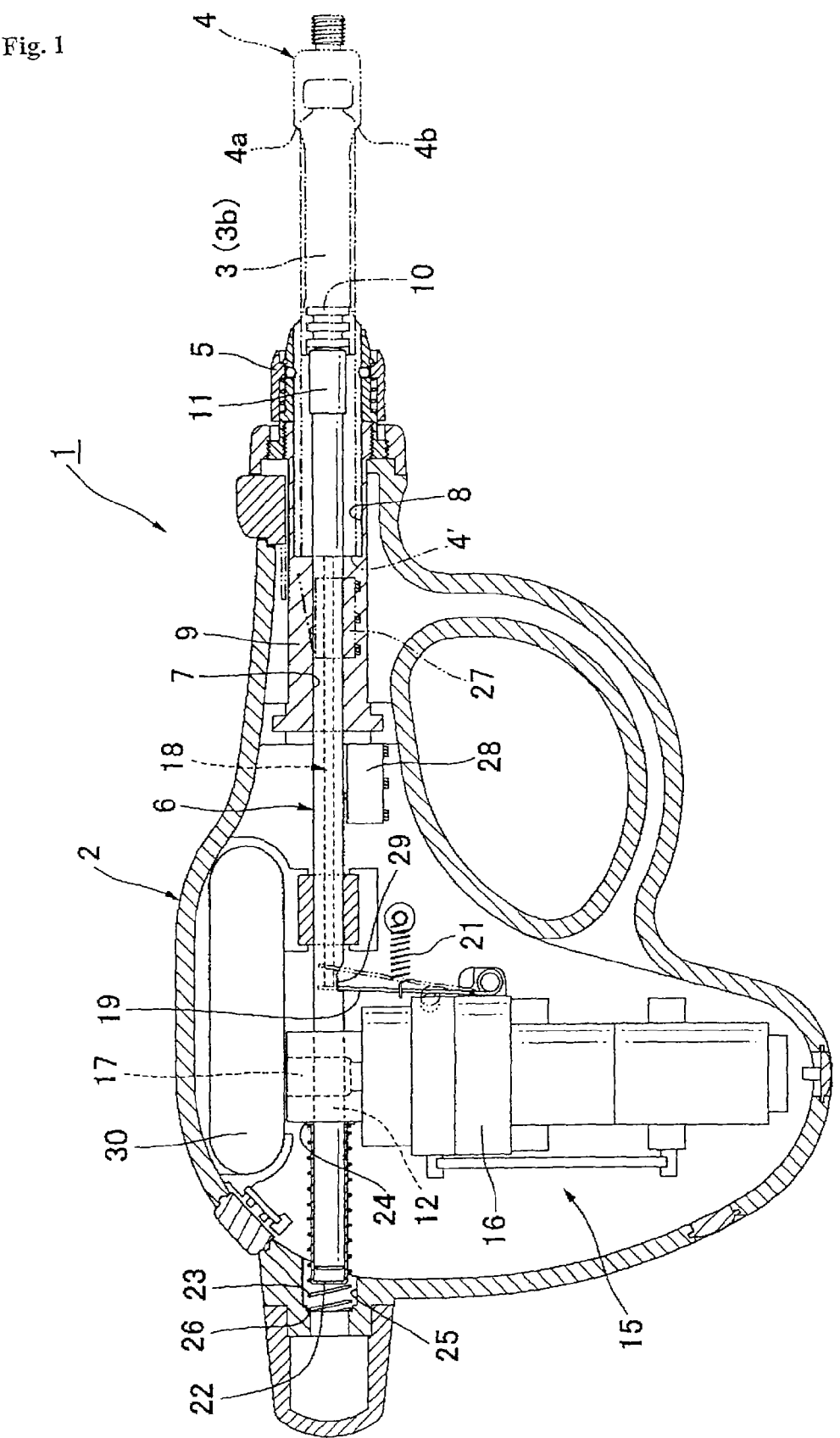
FIG. 1 is a side view in section of a motorized syringe according to the invention, in which a cartridge containing 1.0 ml of anesthetic solution is used.
Figure 2:
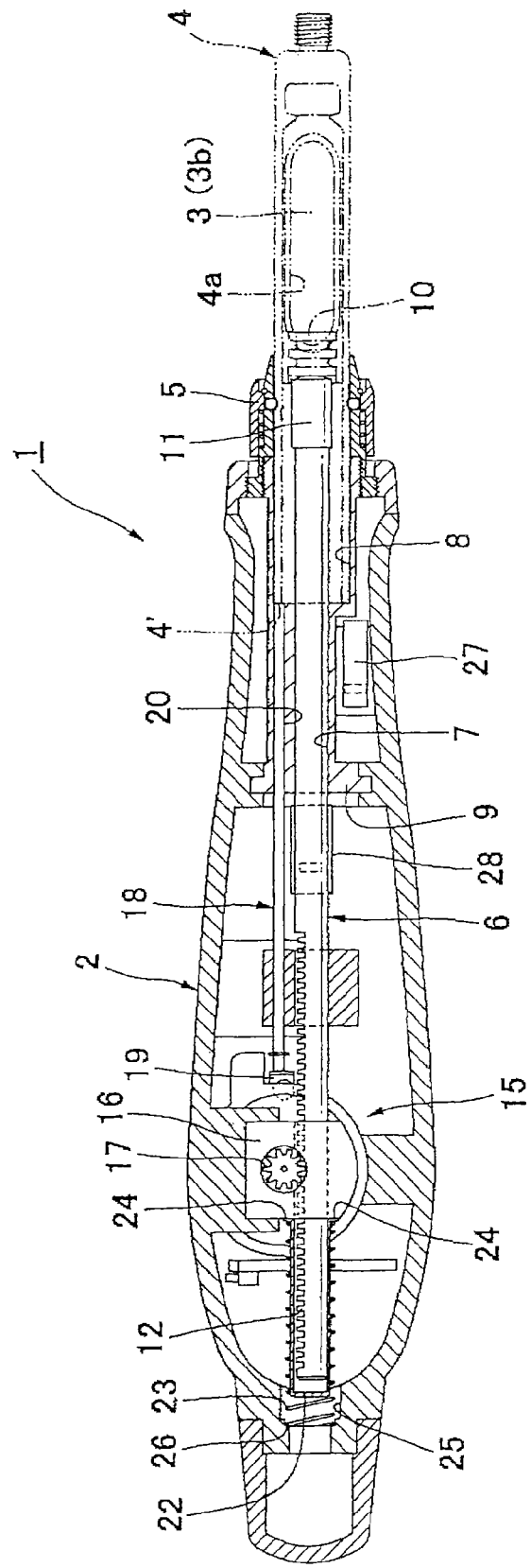
FIG. 2 is a top plan view in section of the motorized syringe of FIG. 1.
Figure 3:
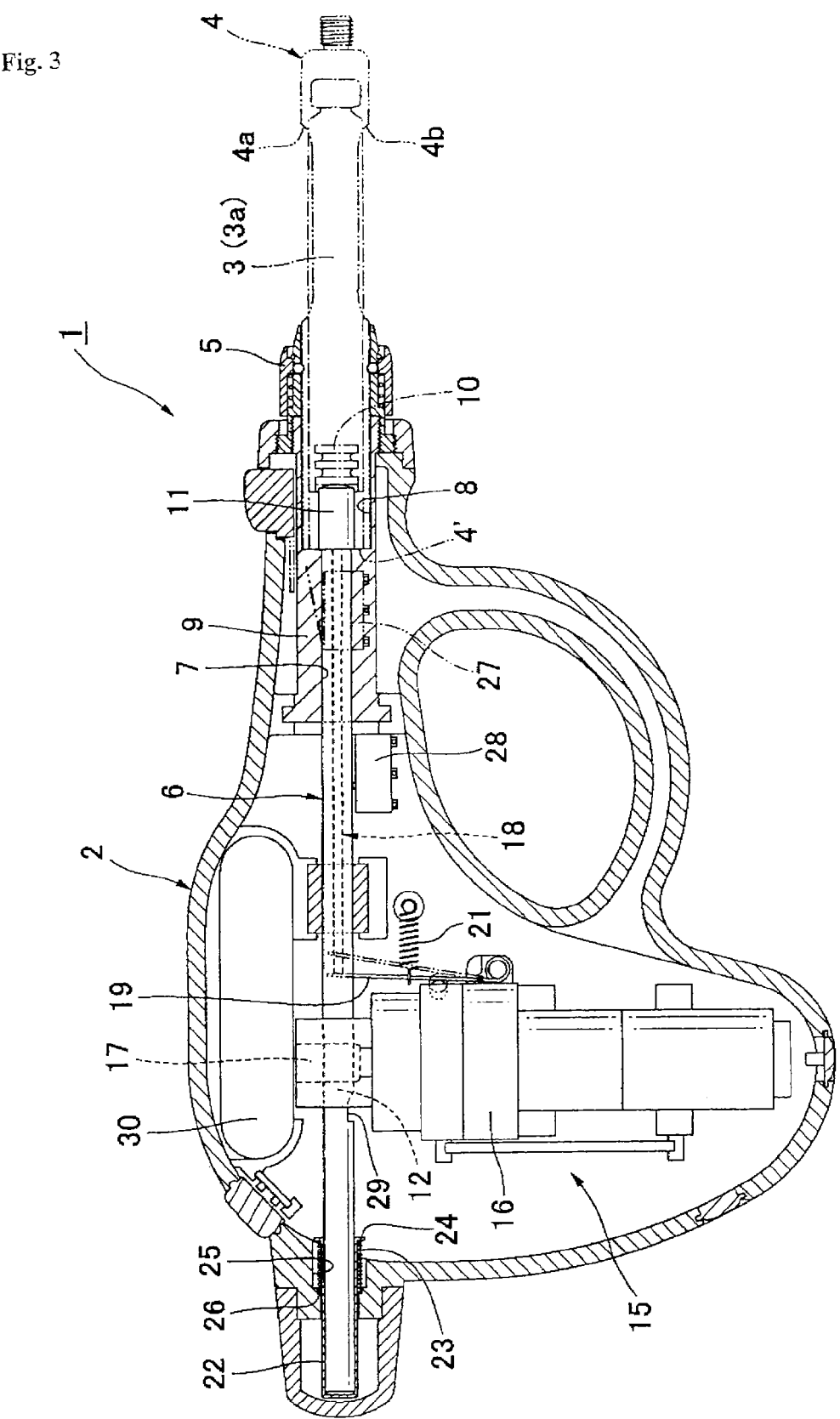
FIG. 3 is a side view in section of the motorized syringe according to the invention, in which a cartridge containing 1.8 ml of anesthetic solution is used.
Figure 4:
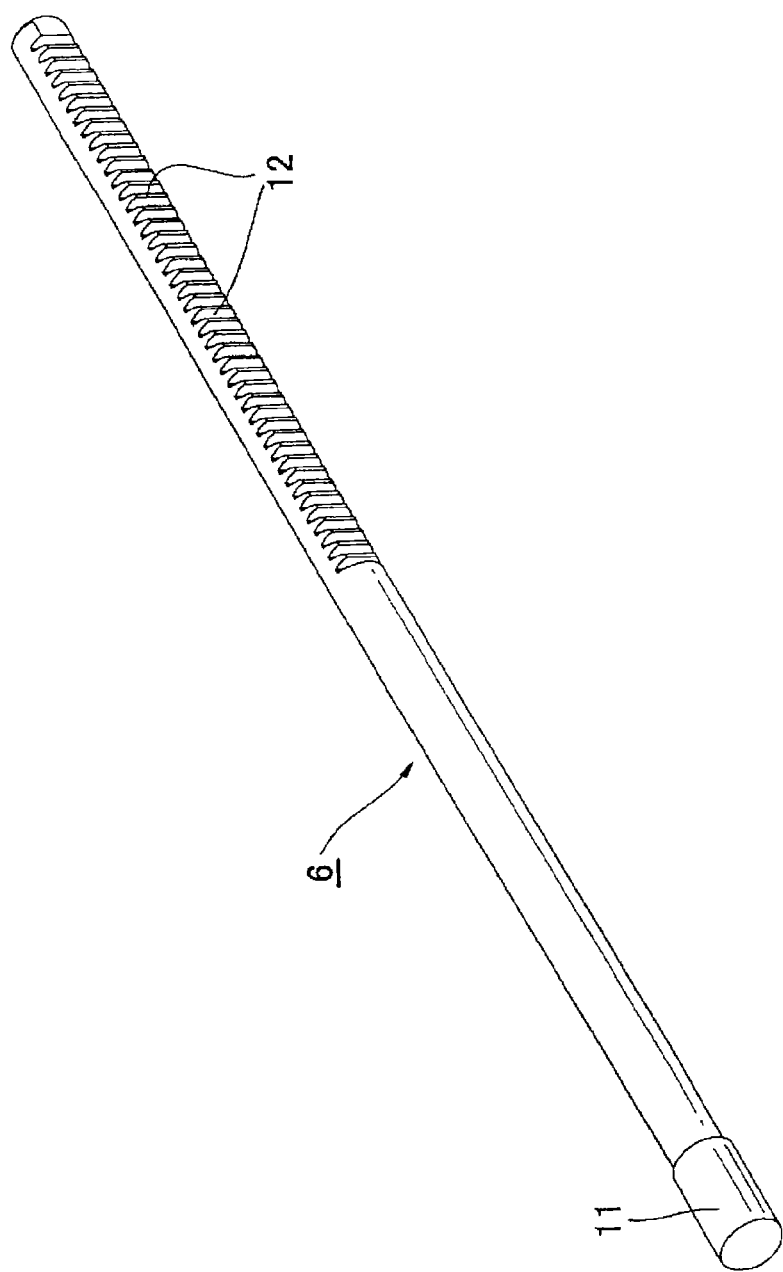
FIG. 4 is a perspective view of a push rod.

Referring to FIG. 1 of the drawings, a motorized syringe 1 according to the invention is shown and comprises a syringe body 2 formed from plastics, and a coupling 5 for detachably connecting to the syringe at its forward end a metallic cartridge holder 4 having an anesthetic solution-filled cartridge 3 loaded therein. The coupling 5 is threadedly affixed to a metallic support member 9 secured to the syringe body 2 having a through-hole 7 through which a metallic round push rod 6 is passed, the support member 9 also having a socket 8 into which the cartridge holder 4 is inserted when it is connected to the syringe body by the coupling 5.

Cartridge holder 4 has windows 4a, 4b formed therein on the opposite sides, the windows being convenient to view the cartridge loaded in the cartridge holder from the exterior. The cartridge holder 4 can be used commonly for both of the cartridges 3b and 3a containing anesthetic solution of 1.0 ml and 1.8 ml, respectively, and is sized such that the rear end of the cartridge holder 4 abuts the bottom of the socket 8 when the cartridge holder 4 is connected to the syringe body by the coupling 5. Push rod 6 is provided at its forward end with a head 11 adapted to abut a plunger rubber plug 10 in the cartridge 3 and formed on one side of its rearward portion with a flat rack 12. The push rod 6 may have a length required for pushing the plunger rubber plug 10 in the 1.0 ml cartridge to deliver anesthetic solution therein completely.

The motorized syringe 1 includes an operating device 15 affixed to the syringe body 2 and including a drive unit 16 including a motor and reduction gear (not shown). A pinion 17 is fixedly connected to an output shaft of the drive unit 16, and is adapted to engage rack 12. Reference numeral 18 indicates a controlling rod adapted to operate a clutch lever 19 from its clutch releasing position to its clutch coupling position in which a clutch (not shown) in the drive unit 16 is coupled, when the controlling rod is pushed with the rear end of the cartridge holder 4 inserted into the socket 8. The controlling rod 18 is passed through a through-hole 20 formed in the support member 9 in juxtaposition with the through-hole 7 for the push rod 6 and moved forwardly into the socket 8 by the clutch lever 19, returning to its clutch releasing position under the action of a coil-like tension spring 21 when the cartridge holder 4 is disconnected from the coupling 5 to remove it from the socket 8. The clutch in the drive unit 16 is released by such operation of the clutch lever 19 so that the power transmission will be cut off to make manual rearward movement of the push rod 6 possible.

There is provided a bottomed sleeve 22 adapted to receive a rear end portion of the push rod 6 in its retracted position. The sleeve 22 preferably may be of a length slightly longer than a difference in length between the 1.0 ml cartridge and the 1.8 ml cartridge. A coil return spring 23 is disposed around the sleeve 22 and abuts at its one end a peripheral flange 24 of the sleeve 22 and at the other end a shoulder 26 in a bore 25 formed in the syringe body 2 at its rear end, to urge the sleeve 22 against a portion of the drive unit 16 in a normal state. In this state, the sleeve 22 is positioned in the vicinity of the rear end face of the push rod 6. Reference numeral 27 indicates a main switch, and 28, a limit switch. When a recess 29 in the push rod 6 faces the switch 28 due to movement of the push rod by a predetermined distance, the switch 28 functions to change from on to off, thereby, stopping the rotation of the motor in the drive unit 16. Reference numeral 30 indicates a battery box which is a power source for the motor and the like.

In the case where the 1.0 ml cartridge 3b is used, it is loaded into the cartridge holder 4, and it is inserted into the socket 8 until the cartridge holder 4 abuts the bottom of the socket 8, thereby connecting the cartridge holder to the syringe body by the coupling 5. In the process of insertion of the cartridge holder, abutment of the plunger rubber plug 10 in the cartridge 3b against the head 11 of the push rod 6 causes the latter to be pushed rearward to such a degree that the rear end face of the push rod 6 is short of the bottom of the sleeve 22, thereby establishing a setting position of the cartridge 3b.

In the case where the 1.8 ml cartridge 3a is used, after it has been loaded in the cartridge holder 4, like the cartridge 3b, the cartridge holder 4 is inserted into the socket 8 until it abuts the bottom of the socket 8, thereby connecting the cartridge holder to the syringe body by the coupling 5. By abutment of the plunger rubber plug 10 in the cartridge 3b against the head 11, the push rod 6 is pushed rearward a distance equal to the difference in length between cartridge 3a and cartridge 3b. At this point, the push rod 6 pushes rearward the sleeve 22 with abutment of the rear end face thereof against the bottom of the sleeve 22 so that the sleeve 22 passes and protrudes through the bore 25. Thus, the coil return spring 23 is compressed. The compressed coil return spring 23 forces the push rod 6 against the plunger rubber plug 10 in the cartridge 3a to establish a setting position of the cartridge 3a.

The motorized syringe is ready for use when a double-head needle (not shown) is attached to the tip of the cartridge holder 4 for communication with the interior of the cartridge. In the case of either cartridge, the motorized syringe is put into operation by the main switch 27. The push rod 6 is advanced by the rack 12 engaged with the pinion 17 which is rotated through the power transmission from the drive unit 16, so that it can push the plunger rubber plug 10 to deliver the anesthetic solution from the cartridge through the needle. In the case of the 1.0 ml cartridge, the linear forward movement of the push rod 6 is performed while coming out of the sleeve 22 which is in the stationary position and ultimately, the end of the push rod 6 reaches a terminal position in which the injection is completed. In the case of the 1.8 cartridge, the force of the compressed coil return spring 23 causes the sleeve 22 to be moved forward together with the push rod 6 until the forward end face abuts the side surface of the drive unit 16. The movement of the sleeve 22 is stopped by abutment with the side surface of the drive unit 16, and the push rod 6 continues to linearly move forward while coming out of the stopped sleeve 22 and ultimately, it reaches the terminal position, like in the case of the 1.0 cartridge, in which the injection is completed.

In the case of either cartridge, the cartridge holder 4 is disconnected from the coupling 5 on completion of the injection, so that it can be removed from the socket 8. At this point, the push rod 6 can freely be pushed back toward the coupling 5 by hand as described hereinbefore. In course of the rearward movement of the push rod, its rear end portion enters the sleeve 22 maintained in the stationary position. As described hereinbefore, in the 1.0 ml cartridge-setting position, the sleeve 22 remains in position without being pushed with the rear end face of the push rod, whereas in the 1.8 ml cartridge-setting position, the sleeve 22 is pushed rearward with the rear end face of the push rod while compressing the return spring. In the case of either cartridge, the forward movement of the push rod, thus, permits the plunger rubber plug in the cartridge to be pushed for delivery of the anesthetic solution from the cartridge through the needle, whereas in the case of the 1.8 ml cartridge, the sleeve can be moved, together with the push rod, under the action of the return coil spring.

According to the invention, the cartridge holder is configured to be used in common for both a 1.0 ml cartridge and a 1.8 ml cartridge, the push rod has a 1.0 ml cartridge-setting position and a 1.8 ml cartridge-setting position drawn back from the 1.0 ml cartridge-setting position, so that the movement of the push rod can end at its common terminal position for 1.0 ml and 1.8 ml cartridges, and due to the fact that the syringe comprises the bottomed sleeve for receiving the rear end portion of the push rod therein when the push rod is pushed back from the common terminal position, the sleeve being pushed rearward with the rear end face of the push rod when the push rod is pushed back to the 1.8 ml cartridge-setting position, and the return spring for moving forward the sleeve together with the push rod upon the forward movement of the push rod, the plunger rubber plug in the 1.8 ml cartridge can be pushed by the push rod the distance required to push the plunger rubber plug in the 1.0 ml cartridge. Thus, the invention can provide a motorized syringe of compact configuration.

DESCRIPTION OF THE REFERENCE NUMERALS

1 motorized syringe
2 syringe body
3 anesthetic solution-filled cartridge
3a 1.8 ml cartridge
3b 1.0 ml cartridge
4 cartridge holder
5 coupling
6 push rod
8 socket
4' rear end face
10 plunger rubber plug
12 rack
15 operating device
16 drive unit
17 pinion
22 bottomed sleeve
23 coil return spring
24 peripheral flange
25 bore
26 shoulder

What we claim is:

1. A motorized syringe for use with two types of dental anesthetic solution-filled cartridges, comprising
   a syringe body,
   a cartridge holder adapted to be connected to said syringe body by means of a coupling, said cartridge being loaded in said cartridge holder,
   a push rod having a rack formed thereon, and a pinion engaged with said rack and adapted to be rotated by a drive unit, the engagement of said rotating pinion with said rack moving said push rod slowly forward, thereby pushing a plunger rubber plug in said anesthetic solution-filled cartridge for delivery of said anesthetic solution from said cartridge through a needle, wherein
   said cartridge holder is configured to be capable of being used in common for both of 1.0 ml and 1.8 ml cartridges,
   said push rod has a 1.0 ml cartridge-setting position and a 1.8 ml cartridge-setting position drawn back from said 1.0 ml cartridge-setting position so that forward movement of said push rod ends at a common terminal position for both the 1.0 ml and 1.8 ml cartridges,
   the syringe comprises a bottomed sleeve adapted to receive a rear end portion of said push rod therein when said push rod is pushed back from said common terminal position, and to be not interfered with by a rear end face of the push rod when the push rod is in the 1.0 ml cartridge-setting position, said sleeve being pushed rearwardly with the rear end face of said push rod when the push rod is pushed back to the 1.8 ml cartridge-setting position, and
   the syringe comprises a return spring for moving forward said sleeve together with said push rod upon its forward movement.

2. The motorized syringe according to claim 1, wherein said return spring is a coil return spring disposed around said bottomed sleeve and abutting at its first end a peripheral flange formed on said sleeve at its forward end, and abutting at its second end a shoulder in a bore formed in said syringe body at its rear end, and said return spring urges said sleeve against a portion of said drive unit in a normal state thereof, so that said sleeve is positioned in proximity to the rear end face of the push rod, and said sleeve protrudes through the bore at the rear end of said syringe body when it is pushed rearwardly with the rear end face of said push rod.

3. The motorized syringe according to claim 1, wherein said sleeve has a length slightly longer than a difference in length between the 1.0 ml cartridge and the 1.8 ml cartridge.

4. The motorized syringe according to claim 2, wherein said sleeve has a length slightly longer than a difference in length between the 1.0 ml cartridge and the 1.8 ml cartridge.

* * * * *